(12) United States Patent
Ferrendelli et al.

(10) Patent No.: US 6,680,331 B2
(45) Date of Patent: Jan. 20, 2004

(54) LACTAM AND THIOLACTAM DERIVATIVES AS ANESTHETIC AND CONSCIOUS SEDATION AGENTS

(75) Inventors: James A. Ferrendelli, Houston, TX (US); Douglas F. Covey, Ballwin, MO (US)

(73) Assignees: Board of Regents, The University of Texas System, Austin, TX (US); Washington University, St. Louis, MO (US)

( * ) Notice: Subject to any disclaimer, the term of this patent is extended or adjusted under 35 U.S.C. 154(b) by 56 days.

(21) Appl. No.: 09/907,547

(22) Filed: Jul. 16, 2001

(65) Prior Publication Data

US 2003/0078283 A1 Apr. 24, 2003

(51) Int. Cl.$^7$ .................... A61K 31/40; A61K 31/4015; A61K 31/402; A61K 31/445; A61K 31/45
(52) U.S. Cl. ....................................... 514/327; 514/424
(58) Field of Search ................................. 514/327, 424

(56) References Cited

U.S. PATENT DOCUMENTS

| | | | |
|---|---|---|---|
| 4,399,145 A | 8/1983 | Graudums et al. | 424/267 |
| 5,776,959 A | 7/1998 | Covey et al. | 514/345 |
| 6,066,666 A | 5/2000 | Covey et al. | 514/424 |

FOREIGN PATENT DOCUMENTS

DE          2609209          9/1976

OTHER PUBLICATIONS

Baker et al., "Synthesis of 3,3–diethylpiperid–2–one," *J. Chem. Soc.*, C:2148, 1967.

Hill et al., "Contribution of Subsaturating GABA Concentrations to IPSCs in Cultured Hippocampal Neurons" *J. of Neuroscience*, 18(14):5103–5111, 1998.

Hill et al., "Inhibition of Voltage–Dependent Sodium Channels by the Anticonvuslant $\mu$–Aminobutyric Acid Type A1 Receptor Modulator, 3–Benzyl–3–Ethyl–2–Piperidinone" *J. Pharmacol. Exp. Ther.*, 285:1303–1309, 1998.

Hill et al., "Effects of anticonvulsant lactams on in vitro seizures in the hippocampal slice preparation." *Epilepsy Research*, 37:121–131, 1999.

Kametani et al., "Alkaloids of Corydalis pallida var tenuis and the structures of pallidine and kikemanine" *J. Chem. Soc.*, C:1060–1064, 1970.

Kircheldorf, "Reactions with silylazides. 7. Trimethylsilyl 4–isocyanato–carboxylates and 4–aminocarboxylic acid N–carboxylic acid anhydrides," *Makromol. Chem.*, 176:57–79, 1975.

Lister, "The use of plus–maze to measure anxiety in the mouse," *Psychopharmacology*, 92:180–185, 1987.

Menezes and Smith, "A mild and facile root to –amino esters," *Synth. Commun.*, 18: 1625–1636, 1988.

Reddy et al., "3,3–Dialkyl– and 3–Alkyl–3– Benzyl–Substituted 2–Pyrrolidinones: A new class of anticonvulsant agents," *J. Med. Chem.*, 39:1898–1906, 1996.

Reddy et al., "Synthesis and Anticonvulsant Activities of 3,3–Dialkyl– 3–Alkyl–3–benzyl–2–piperidinones ($\delta$–Valerolactams) and Hexahydro–2H–azepin–2–ones ($\epsilon$–Caprolactams)," *J. Med. Chem.*, 40:44–49, 1997.

Stamm et al., "Reactions with aziridines. XXII. One step synthesis of pyrrolidones by amidothylation of simple esters with N–acylaziridines," *Chem. Ber.*, 114:32–48, 1981.

*Primary Examiner*—Phyllis G. Spivack
(74) *Attorney, Agent, or Firm*—Fulbright & Jaworski L.L.P.

(57) ABSTRACT

This invention relates to lactam and thiolactam derivatives having useful anesthetic and conscious sedation activity. Particularly useful compounds include the diethyl lactams such as 3,3-diethyl-2-pyrrolidinone. Methods for using these compounds and pharmaceutical compositions containing these compounds are provided.

16 Claims, No Drawings

LACTAM AND THIOLACTAM DERIVATIVES AS ANESTHETIC AND CONSCIOUS SEDATION AGENTS

The government may own rights in the present invention pursuant to grant number 5 PO1 NS14834 from the National Institute of Health.

BACKGROUND OF THE INVENTION

I. Field of the Invention

The present invention relates generally to the field of anesthesiology. More particularly, it provides for the therapeutic application of lactam and thiolactam derivatives for anesthesia and conscious sedation activity.

II. Description of Related Art

There are numerous compounds presently used to provide anesthesia. Goodman and Gilman (1996) provide an overview of the field of anesthesiology as understood by those skilled in the art. However, many of the compounds in use as general anesthetic agents or for conscious sedation have a variety of problems. Compounds which are not water soluble are difficult to administer by conventional routes. Tolerances develop for some anesthetics such as benzodiazepines and opioids. Also, these compounds tend to have substantial adverse side effects and are potentially addictive. The slow onset of anesthesia is another problem with many anesthetic agents. Preferred anesthetics would have a rapid, almost instantaneous onset with a duration that can be controlled by the dose of anesthetic provided to a patient.

Sulphobenzoic acid lactam compounds for use as sedative-tranquilizing properties and hypno-anesthetics have been reported (U.S. Pat. No. 4,399,145). However, these compounds have low water solubility and a rapid onset of anesthetic properties is not mentioned.

It would therefore be advantageous to have water soluble compounds with anesthetic properties that are safe, have a rapid onset and a dose dependent duration.

SUMMARY OF THE INVENTION

Thus, the present invention contemplates therapeutic applications using lactam and thiolactam derivatives having useful anesthetic and conscious sedation activity. The lactams and thiolactams will be provided in an amount sufficient to produce anesthesia or conscious sedation.

The present invention provides a method for inducing anesthesia or conscious sedation in a patient comprising administering to the patient a composition comprising a compound having the formula:

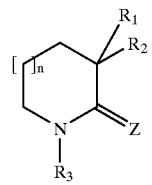

or pharmaceutically acceptable salts thereof wherein: n is 0 or 1; Z is an O or S; and $R_1$, $R_2$, and $R_3$ are independently selected from the group consisting of H, an optionally substituted alkyl or alkenyl group, and an optionally substituted phenylmethyl group, with the exceptions that: $R_1$ and $R_2$ cannot both be H; when one of $R_1$ or $R_2$ is H or a methyl group, the other of $R_1$ or $R_2$ cannot be a methyl or ethyl group; and when n=1, $R_1$ and $R_2$ cannot both be ethyl.

Preferably, the compound has a water solubility of at least 0.1 g per 1.0 g of water, at least 0.5 g per 1.0 g of water or even more preferably, at least 1.0 g per 1.0 g of water. The composition may comprise additional water or buffer. The compound may be administered intravenously, orally, rectally, intramuscularly, subcutaneously, through an inhalation administration, or through any other method known in the art for delivery of anesthesia or conscious sedation therapy.

It is an aspect of the current invention that the compound is given at a dosage of 1–1000 mg/kg, 100–1000 mg/kg, or from 10–100 mg/kg. The compound may be an enantiomerically enriched mixture and preferably comprises 3,3-diethyl-2-pyrrolidinone.

An aspect of the current invention is that the onset of anesthesia is rapid, where the compound produces an onset of anesthesia in less than 5 minutes, 4 minutes, 3 minutes, 2 minutes, 1 minute, 45 seconds, 30 seconds, 20 seconds, 10 seconds, or 5 seconds after administration.

DESCRIPTION OF ILLUSTRATIVE EMBODIMENTS

I. The Present Invention

The present invention provides drugs for general anesthesia and conscious sedation. More particularly, the invention relates to 3-substituted and 3,3-disubstituted 2-pyrrolidinones (α-substituted and α,α-disubstituted γ-butyrolactams), and 3-substituted and 3,3-disubstituted 2-piperidinones (α-substituted and α,α-disubstituted γ-valerolactams) and thiolactam analogs having anesthesia and conscious sedation properties.

II. Lactams and Thiolactams

Anesthetic compounds of this invention are lactams and thiolactams which can be described by the general formula:

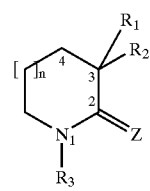

(I)

where n is 0 or 1; Z is an oxygen or a sulfur atom; and $R_1$, $R_2$ and $R_3$ are independently selected from the group consisting of H, an optionally substituted alkyl or alkenyl group, and an optionally substituted phenylmethyl group; with the exceptions that: $R_1$, $R_2$ cannot both be H; and when one of $R_1$ or $R_2$ is H or methyl, the other of $R_1$ or $R_2$ cannot be a methyl or ethyl group.

Anesthetic compounds of formula I of this invention include lactams (formula II) and thiolactams (formula III) where n, $R_1$, $R_2$, and $R_3$ are as defined for formula I.

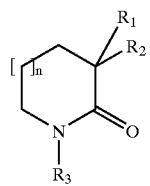

(II)

-continued

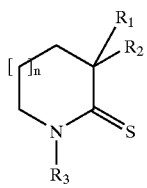
(III)

where lactams of formula II are generally preferred over thiolactams of formula III.

Compounds of formula I include both five- and six-member ring compounds which are exemplified by pyrrolidinones of formula IV and piperidinones of formula V:

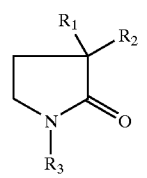
(IV)

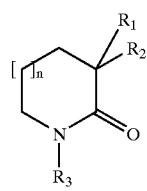
(V)

where $R_1$, $R_2$, and $R_3$ are as defined above for formula I.

In specific aspects, this invention includes compounds of formula I and II where one of $R_1$, or $R_2$, is an optionally substituted phenylmethyl group as exemplified in the lactams and thiolactams of formula VI:

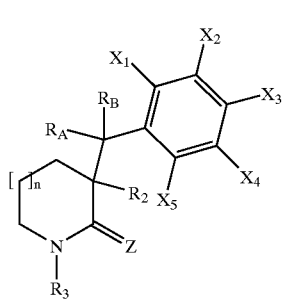
(VI)

where n, Z, $R_1$, $R_2$ and $R_3$ are as defined above for formulae I and II and $R_A$, $R_B$, $X_1$, $X_2$, $X_3$, $X_4$ and $X_5$ are hydrogens or substitutents, as defined below.

In formulas I–VI, one or more of $R_1$, $R_2$ and $R_3$ can be optionally substituted alkyl, alkenyl or phenylmethyl groups. Substitutents include, among others, halogen atoms, a carbonyl, cyano, hydroxy, mercapto, amino or nitro group, alkynyl, alkoxy, thioalkoxy, alkyl amine, haloalkyl or haloalkenyl group, particularly those substituents having up to about 6 carbon atoms, and preferably those substituents having from one to about 4 carbon atoms and alkyl, alkenyl or alkynyl groups substituted with one or more carbonyl, cyano, hydroxy, mercapto, amino or nitro groups, particularly those substituents having up to about 6 carbon atoms and preferably those substitutents having from 1 to about 4 carbon atoms. Preferred substitutents are those that increase the water solubility of the compounds. Compounds of formulas I–VI that are water soluble are preferred.

Optionally substituted alkyl and alkenyl groups of $R_1$, $R_2$ and $R_3$, include those which are straight-chain, branched or contain an alicyclic group, e.g., cyclopropyl, cyclobutyl, cyclohexyl, perfluoroalicyclic groups and the like.

Optionally substituted alkyl and alkenyl groups include haloalkyl and haloalkenyl groups, particularly those having from 1 to about 4 carbon atoms. Preferred haloalkyl groups and haloalkenyl groups are fluoroalkyl and fluoroalkenyl groups, respectively.

As illustrated in formulas VI, phenylmethyl groups can be substituted at the methyl carbon or on the phenyl ring. For optionally substituted phenylmethyl groups of any of $R_1$, $R_2$ and $R_3$, substituents include halogen atoms, a carbonyl, cyano, hydroxy, mercapto, amino or nitro group, an alkyl, alkenyl, alkynyl, alkoxy, thioalkoxy, alkyl amine, haloalkyl or haloalkenyl group, particularly those groups having up to about 6 carbon atoms, preferably those groups having 1 to 4 carbon atoms and alkyl or alkenyl groups substituted with one or more carbonyl, cyano, hydroxy, mercapto, amino or nitro groups, particularly those groups having up to about 6 carbon atoms and preferably those having 1 to 4 carbon atoms. Generally preferred substituents for $R_1$, $R_2$ and $R_3$ groups are atoms or chemical moieties or groups that do not interfere with anesthetic or conscious sedation activity of the compound.

More specifically with respect to phenylmethyl group substituents and particularly substituents $R_A$, $R_B$, $X_1$, $X_2$, $X_3$, $X_4$ and $X_5$, these substituents, independently of one another, can, for example, be selected from the group consisting of a hydrogen, a halogen, an alkyl, an alkenyl, an alkoxy, an alkylamino, a mercapto, a thioalkyl, a thioalkoxy, a haloalkoxy, a haloalkenyl, a hydroxy, an amino, a nitro or a cyano group. Substituents include those having up to about 6 carbon atoms, particularly alkyl or alkenyl groups. Generally preferred substituents are those having from one to about 4 carbon atoms, particularly alkyl and alkenyl groups.

The substituents on the phenylmethyl group are illustrated by one or more of the following groups in any of the ortho-, meta- or para-positions of the phenyl ring and/or at either or both positions on the methyl carbon: F, Cl, Br, I, acetyl, alkyl (C1 to about C4), alkenyl (C1 to about C4), alkynyl (C1 to about C4), alkoxyl (C1 to about C4), haloalkyl (C1 to about C4), haloalkenyl (C1 to about C4), amino, mono- and dialkylamino (C1 to about C4), cyano, hydroxy, mercapto, nitro, and carboxy.

Preferred haloalkyl and haloalkenyl substituents for phenylmethyl groups are fluoroalkyl and fluoroalkenyl groups having up to about 4 carbon atoms. Generally preferred substituents for phenylmethyl groups are fluorines and small alkyl or alkenyl groups having from 1 to about 4 carbon atoms. The phenyl ring of the phenylmethyl group can be substituted at any position.

Alkyl substituents in the above structural formulae are illustrated by methyl, ethyl, propyl, isopropyl, iso-butyl, sec-butyl, and tert-butyl, cyclopropyl and cyclobutyl. The fluoroalkyl substituents are illustrated by trifluoromethyl, 1,1-difluoroethyl, 2,2,2-trifluoroethyl, 1-trifluoromethylethyl, and 1-methyl-1-trifluoromethylethyl.

When the $R_1$ and $R_2$ substituents are different, the compounds of the above structural formulae (I–VI) exist as (+)- and (−)-enantiomers. Such compounds of this invention are useful either in the racemic (+/−)-form or the nonracemic (+)- or-(−)-enantiomeric forms.

Anesthetic compounds of this invention include those of the above formulae in which $R_3$ is selected from the group consisting of a hydrogen, an alkyl or alkenyl group having from one to about 6 carbon atoms and a phenylmethyl or an optionally substituted phenylmethyl group. Also included are those compounds in which $R_3$ is an alkyl or alkenyl group having from one to about four carbon atoms, those where $R_3$ is a hydrogen, methyl or ethyl group, those where $R_3$ is a phenylmethyl group and those where $R_3$ is a hydrogen.

Anesthetic compounds of this invention specifically include those where Z is oxygen. In particular, this invention includes 3-mono- and 3,3-disubstituted 2-pyrrolidinones, where Z is oxygen and n=0 and 3-mono and 3,3-disubstituted 2-piperidinones, where Z is oxygen and n=1 with the $R_1$, $R_2$ and $R_3$ substitutents listed above in formulae I and II.

Anesthetic compounds of this invention include those in which $R_1$ is a different group from $R_2$.

Anesthetic compounds of this invention include those compounds of formula I in which one of $R_1$ or $R_2$ is a phenylmethyl or substituted phenylmethyl group. Also included are those compounds where one of $R_1$ or $R_2$ is a phenylmethyl or substituted phenylmethyl group and the other is a hydrogen or an alkyl having from 2 to about 4 carbon atoms.

Preferred anesthetic compounds of formula I are those in which $R_1$ and $R_2$ are selected from the group consisting of a hydrogen, an alkyl or alkenyl having two to about four carbon atoms and a phenylmethyl group. Also preferred are those in which $R_3$ is a hydrogen, methyl, ethyl or phenylmethyl group. More preferred $R_3$ groups are those having two or fewer carbon atoms.

Several 2-pyrrolidinone and 2-piperidinone derivatives that can be described by formulas IV and V have been reported including 3-methyl-2-pyrrolidinone (Menezes et al., 1988; Khoukhi et al., 1987; Adams et al., 1959), 3-ethyl-2-pyrrolidinone (Kametani et al., 1970; Cummings et al, 1964; Brunner et al., 1951), 3-(2-methylpropyl)-2-pyrrolidinone (Geurtis, 1977; Ger. Offen. 2,609,209), 3-butyl-2-pyrrolidinone (Sinnerich et al., 1968), 3-phenylmethyl-2-pyrrolidinone; (Menezes et al., 1988; Bentz et al., 1987; Werry et al., 1989), and 3,3-dimethyl-2-pyrrolidinone (Stamm et al., 1981); Kricheldorf, 1975). 2-Piperidinone derivatives include 3-methyl-2-piperidinone (Khoukhi et al., 1987); 3-ethyl-2-piperidinone (Koelsch et al., 1943); 3-propyl-2-piperidinone (U.S. Pat. No. 4,420, 568), 3-(2-methylpropyl)-2-piperidinone (Rodriguez et al., 1992), 3-phenylmethyl-2-piperidinone and (EP 435,387), 3,3-dimethyl-2-piperidinone (Mileo et al., 1968). EP 435, 387 reports lactams as potential intermediates in the synthesis of piperidine derivatives that are useful as fungicides. Certain 3-mono- and 3,3-disubstituted lactams have been shown to significantly enhance GABA neuronal inhibition and are significantly more active anticonvulsant and anxiolytic agents than prior art lactones and thiolactones (U.S. Pat. Nos. 6,066,666 and 5,776,959, Hill et al., 1999, Hill et al., 1998(a–b), herein incorporated by reference). However, these derivatives have not been reported to show anesthetic or conscious sedation activity. One compound, 3,3-diethyl-2-piperidinone (Baker et al., 1967) has been reported to have only weak sedative activity in mice.

a. Representative Compounds

Representative anesthetic compounds of this invention are 3,3-diethyl-2-pyrrolidinone, 3-ethyl-3-phenylmethyl-2-pyrrolidinone, 3-methyl-3-phenylmethyl-2-pyrrolidinone, 3-phenylmethyl-2-pyrrolidinone, 3-ethyl-3-phenylmethyl-2-piperidinone, 3-methyl-3-phenylmethyl-2-piperidinone and 3-phenylmethyl-2-piperidinone, 3-ethyl-3-isopropyl-2-pyrrolidinone; 3-ethyl-3-isopropyl-2-piperidinone; 3-isopropyl-3-phenylethyl-2-piperidinone; 3-ethyl-3-methyl-2-piperidinone; 3-isopropyl-3-methyl-2-piperidinone, 3,3-isopropyl-2-piperidinone, 3-n propyl-3-ethyl-2-piperidinone, 3,3-n propyl-2-piperidinone and 3-n propyl-3-methyl-2-piperidinone.

Additional representative compounds of this invention include, among others: 3-(p-fluorophenylmethyl)-2-pyrrolidinone, 3-(p-fluorophenylmethyl)-2-piperidinone, 3-(p-fluorophenylmethyl)-3-methyl-2-pyrrolidinone, 3-(p-fluorophenylmethyl)-3-methyl-2-piperidinone; 3-n-propyl-2-pyrrolidinone, 3-isopropyl-2-pyrrolidinone, 3-tert-butyl-2-pyrrolidinone, 3-n-butyl-2-pyrrolidinone, 3-sec-butyl-2-pyrrolidinone, 3-n-propyl-2-piperidinone, 3-isopropyl-2-piperidinone, 3-tert-butyl-2-piperidinone, 3-n-butyl-2-piperidinone, 3-sec-butyl-2-piperidinone; 3,3-diethyl-1-methyl-2-pyrrolidinone, 3-ethyl-1-methyl-3-phenylmethyl-2-pyrrolidinone, 1,3-dimethyl-3-phenylmethyl-2-pyrrolidinone, 1-methyl-3-phenylmethyl-2-pyrrolidinone, 3,3-diethyl-1-methyl-2-piperidinone, 3-ethyl-1-methyl-3-phenylmethyl-2-piperidinone, 1,3-dimethyl-3-phenylmethyl-2-piperidinone, 1-methyl-3-phenylmethyl-2-piperidinone, 3-ethyl-1,3dimethyl piperidinone; 3,3-diethyl-1-phenymethyl-2-pyrrolidinone, 1,3-diphenylmethyl-3-ethyl-2-pyrrolidinone, 1,3-diphenylmethyl-3-methyl-2-pyrrolidinone, 1,3-diphenylmethyl-2-pyrrolidinone, 3,3-diethyl-I-phenylmethyl-2-piperidinone, 1,3-diphenylmethyl-3-ethyl-2-piperidinone, 1,3-diphenylmethyl-3-methyl-2-piperidinone, 1,3-diphenylmethyl-2-piperidinone, 3-ethyl-3-methyl-1-phenylmethyl-2-piperidinone. Additional representative compounds of this invention also include: 3,3-diethyl-2-pyrrolidinethione, 3-ethyl-3-phenylmethyl-2-pyrrolidinethione, 3-methyl-3-phenylmethyl-2-pyrrolidinethione, 3-phenylmethyl-2-pyrrolidinethione, 3,3-diethyl-2-piperidinethione, 3-ethyl-3-phenylmethyl-2-piperidinethione, 3-methyl-3-phenylmethyl-2-piperidinethione and 3-phenylmethyl-2-piperidinethione.

Preferred compounds of this invention are 3,3-diethyl-2-pyrrolidinone, and other compounds of formulae I–VI which are water soluble.

Pharmaceutical compositions of this invention are those having one or more of the compounds of formulae I–VI in an amount effective for anesthetic or conscious sedation effects in a mammal. Preferred pharmaceutical compositions of this invention include those having one or more of the 3-mono and 3,3-disubstituted compounds of formula I in an amount effective for anesthetic or conscious sedation effects in a mammal.

b. Synthesis of the Lactams and Thiolactams

Methods of synthesis of the compounds of formula I–VI are described in U.S. Pat. Nos. 6,066,666 and 5,776,959. Compounds of formula I including 5- and 6-member ring compounds of formulas II and III, respectively, can be readily prepared following the guidance provided in U.S. Pat. Nos. 6,066,666 and 5,776,959 or using synthetic methods well-known in the art of organic synthesis. Synthetic methods well-known in the art can be readily modified and/or adapted, for example, by routine choice of starting materials, reaction conditions, reagents and/or purification methods to synthesize the compounds of formulas I–VI.

For example, the 2-pyrrolidinone derivatives of this invention can be prepared by converting an alkanoic ester $R_1,R_2$ HCCOOR$_3$ into a -cyano alkanoic ester after which the cyano group is reduced to an amino group which cyclizes in situ to yield a 3-substituted 2-pyrrolidinone. Alternatively, a $CH_2=CHCH_2$—group is added to an alkanoic ester $R_1$, $R_2$ HCCOOR$_3$ and then the terminal carbon of the alkenyl group is removed to obtain an aldehyde group. The aldehyde group is converted to an oxime group which is then reduced to obtain an amino group which cyclizes in situ to yield a 2-pyrrolidinone derivative.

Thiolactams can be prepared by treating the analogous lactams with either phosphorus pentasulfide or Lawesson's reagent, for example, by methods described by Bodine et al. (1982) and Potts et al. (1993). Thiolactams of formula I can be prepared by these methods or by art-known modifications or adaptations thereof.

Compounds of formulae I and II with R$_1$, R$_2$ and R$_3$ that are hydrogens or optionally substituted alkyl, alkenyl or phenylmethyl groups can be readily synthesized by reference to methods disclosed herein as in view of methods well-known in the art. All these lactams and thiolactams and derivatives with various R$_1$, R$_2$ and R$_3$ as well as with any phenylmethyl group substitutents R$_A$, R$_B$, X$_1$, X$_2$, X$_3$, X$_4$, and X$_5$ can be readily synthesized using methods described herein in combination with well-known synthetic methods or routine modifications and adaptations of these methods.

III. Anesthetics

The lactams and thiolactam derivatives of this invention can be used for anesthesia and conscious sedation. Surgical and other medical procedures frequently require the application of general anesthesia to a patient. General anesthesia usually includes two or more of analgesia, hypnosis (sedation, amnesia, loss of consciousness), inhibition of sensory and autonomic reflexes, and skeletal muscle relaxation.

The ideal anesthetic is easily administered to the patient, induces anesthesia smoothly and rapidly, permits rapid recovery as soon as the administration of the drugs is ceased, and has no adverse side effects. There are three basic types of anesthesia: local, regional and general anesthesia.

Local anesthesia is given to temporarily stop the sense of pain in a particular area of the body. A patient remains conscious during a local anesthetic. A local anesthetic can be administered topically or via injection to the site. However, when a large area needs to be numbed, or if a local anesthetic injection will not penetrate deep enough, Regional anesthetics will be used.

Regional anesthesia will numb the portion of the body which will be operated on. Usually local anesthetic is injected in the area of nerves that provide feeling to that site or region. There are several forms of regional anesthetics, including spinal anesthetic and epidural anesthetic. Spinal anesthetics are injected into the fluid in the spinal canal and are used to numb lower abdominal, pelvic, rectal or lower extremity regions. Epidural anesthetics are also commonly used for surgery of the lower limbs. It is commonly used as an anesthetic during labor. A thin catheter is placed in the "epidural" space, located in the middle and lower back outside of the spinal space.

General anesthesia causes a patient to be unconscious during a surgical procedure. The anesthetic is usually administered by inhalation through a breathing mask or tube, or administered through an intravenous line. Often, a breathing tube is inserted into the windpipe to maintain proper breathing during surgery because of the reduction in respiratory function caused by the anesthetic. (www.srhs.com/clinical/surgery/anesthesia.htm).

Side effects such as intraoperative vomiting, hypotension, cardiac arrhythmias, respiratory or cardiovascular depression, dysphoria, decrease in cognition and changes in mood are common with anesthetics.

a. Conscious Sedation

The lactams and thiolactams may be used to induce conscious sedation in a patient. Conscious sedation is similar to anesthesia in the minimization of pain and discomfort. However, the patient is in an altered state of consciousness and aware of the procedure. Patients who receive conscious sedation usually are able to speak and respond to verbal cues and communicate any discomfort experienced during the surgery or other procedure. A brief period of amnesia may erase any memory of the procedure. Conscious sedation is administered during procedures such as breast biopsy, vasectomy, minor foot surgery, minor bone fracture repair, plastic/reconstructive surgery, dental prosthetic/reconstructive surgery and endoscopy. Conscious sedation allows patients to recover quickly and resume normal daily activities in a short period of time compared to general anesthesia.

Neuroleptanalgesia is a state in which the patient becomes completely disinterested and detached from the environment without loss of consciousness or the ability to obey commands or communicate with others. This is useful during short procedures requiring full patient cooperation, and can be achieved with some opioids by administering a dosage of less than would be required for general anesthesia. The most common drug combination used here is InnovarR-: fentanyl+droperidol. This combination may be used with nitrous oxide to provide unconsciousness or complete general anesthesia. In this case, the procedure has been termed neuroleptanesthesia. As used herein, the term conscious sedation includes neuroleptanalgesia and the term anesthesia includes neuroleptanesthesia.

IV. Pharmaceutical Preparations

Pharmaceutical compositions of the present invention comprise an effective amount of one or more lactam or thiolactam, such as diethyl lactam or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one lactam or thiolactam or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

An advantage of the lactams and thiolactams of the current invention is the high solubility of the compounds in water. Aqueous solutions are the preferred pharmaceutically acceptable carriers for the anesthetics and conscious sedation compounds of the current invention.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329, incorporated herein by reference). Except insofar as any conventional carrier is incompatible with the active ingredient, its use in the therapeutic or pharmaceutical compositions is contemplated.

The lactam or thiolactam may comprise different types of carriers depending on whether it is to be administered in solid, liquid or aerosol form, and whether it need to be sterile for such routes of administration as injection. The present invention can be administered intravenously, orally, topically, locally, by inhalation (e.g. aerosol inhalation), injection, infusion, continuous infusion, localized perfusion bathing target cells directly, via a catheter, via a lavage, via a suppository, in cremes, in lipid compositions (e.g., liposomes), intradermally, intraarterially, intraperitoneally, intralesionally, intracranially, intraarticularly, intraprostaticaly, intrapleurally, intratracheally, intranasally, intravitreally, topically, intramuscularly, intraperitoneally, subcutaneously, subconjunctival, intravesicularlly, intrapericardially, intraumbilically, intraocularally, or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

Continuous infusion refers to infusions such as intravascular or intrathecal infusions, that provide a continuous drug dosage over a period of time. Continuous infusion can also be achieved using a biologically-compatible device such as a pump system or an in vivo insertable chemical matrix containing the lactam or thiolactam.

In certain embodiments, pharmaceutical compositions may comprise, for example, at least about 0.01 mg/g of body weight of the lactam or thiolactam. In other embodiments, the an active compound may comprise between about 0.1% to about 75% of the weight of the unit, or between about 2% to about 20%, for example, and any range derivable therein. In other non-limiting examples, a dose may also comprise from about 100 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 300 milligram/kg/body weight, about 350 milligram/kg/body weight, about 400 mg/kg/body weigh, about 450 mg/kg/body weigh, about 500 mg/kg/body weigh, about 600 mg/kg/body weigh, about 700 mg/kg/body weigh, about 800 mg/kg/body weigh, about 900 mg/kg/body weigh, about 1000 mg/kg/body weigh, about 2000 mg/kg/body weigh to about 5000 mg/kg/body weight or more per administration, and any range derivable therein. In non-limiting examples of a derivable range from the numbers listed herein, a range of about 350 mg/kg/body weight to about 800 mg/kg/body weight, about 50 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g. methylparabens, propylparabens), chlorobutanol, phenol, sorbic acid, thimerosal or combinations thereof.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Parenteral administration is generally by injection, whether subcutaneously, intramuscularly, or intravenously. Injectables can be prepared in conventional forms, either as solutions or suspensions in liquid prior to injections or as emulsions. Suitable pharmaceutical carriers or excipients include water, saline, dextrose, glycerol, and the like. If desired, the pharmaceutical compositions may also include minor amounts of nontoxic auxiliary substances, such as wetting or emulsifying agents, pH-buffering agents, and so forth.

For oral administration, the active ingredient is generally administered as a syrup, capsule, or tablet, and pharmaceutically nontoxic compositions are formed using the normally employed excipients, such as pharmaceutical grades of mannitol, lactose, starch, magnesium stearate, talcum, cellulose, magnesium carbonate, and so forth. The compositions include sustained release formulations and contain about 10–95% active ingredient with the remainder carrier, as a general rule.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

V. Combinational Therapy and Co-Induction

It is an aspect of this invention that the lactam or thiolactam anesthetic or conscious sedation agent can be used in combination with another agent. When the other agent is another anesthetic, this is termed co-induction. Co-induction of anesthesia is a common technique that exploits drug interaction, particularly synergism between drugs. Co-induction can produce improvement in all phases of anesthesia, including induction, maintenance and recovery (Whitwam, 1995). The lactam or thiolactam may be administered simultaneously with the other agent or may precede or follow the other agent treatment by intervals ranging from minutes to hours.

In embodiments where the other agent is administered to the patient, one would generally ensure that a significant period of time did not expire between the time of each delivery, such that the agent would still be able to exert an advantageously combined effect on the patient. For example, in such instances, it is contemplated that one administer the anesthetic to the patient using with two, three, four or more modalities substantially simultaneously (i.e., within less than about a minute) as the lactam or thiolactam. In other aspects, one or more agents may be administered within of from about 1 minute, about 2 minutes, about 3 minutes, about 5 minutes, about 10 minutes, about 20 minutes about 30 minutes, about 45 minutes, about 60 minutes, about 2 hours, about 5 hours, about 10 hours or more prior to and/or after administering the lactam or thiolactam. In some situations, it may be desirable to extend the time period for treatment significantly, however, where days lapse between the respective administrations.

Various combinations may be employed, the lactam or thiolactam is "A" and the secondary agent, such as an propofol or halothane, is "B":

conjunction with the word "comprising", the words "a" or "an" may mean one or more than one. As used herein "another" may mean at least a second or more.

VI. Examples

The following example is included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of Diethyl Lactam

Preparation of 3,3-diethyl-2-pyrrolidinone (Preparation of Ethyl 2-cyanomethyl-2-ethylbutanoate)

A solution of ethyl 2-ethylbutyrate (21.60 g, 150 mmol) in THF (25 mL) was added dropwise to a solution of lithium diisopropylamide prepared by treating diisopropylamine (16.67 g, 165 mmol) in dry THF (150 mL) with butyllithium in hexanes (2.5M, 66 mL, 165 mmol) at −78° C. for 1 h in a nitrogen atmosphere. The resulting mixture was stirred at −78° C. for 1 h, then a solution of bromoacetonitrile (21.60 g, 180 mmol) in THF (50 mL) was introduced slowly over

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the lactam or thiolactam anesthetic or conscious sedation molecule of this invention.

The second anesthetic or conscious sedation agent with which the lactam or thiolactam of the present invention may be combined may be either an inhalational or intravenous anesthetic agent. Agents commonly used in the co-induction of anesthesia include midazolam, fentanyl, sufentanil, alfentanil and propofol (Whitwam, 1995). Inhalational anesthetic agents include, but are not limited to nitrous oxide ($N_2O$), halothane, enflurane, isoflurane, desflurane and sevoflurane. Intravenous anesthetic agents and balanced anesthesia agents include, but are not limited to ultrashort-acting barbiturates (thiopental sodium, thiamylal sodium, methohexital sodium), benzodiazepines (diazepam, midazolam, opioid analgesics (morphine, fentanyl, sufentanil, droperidol (an antipsychotic drug; non-opioid), nalbuphinem or alfentanil), other agents include ketamine, propofol and etomidate and local drugs (benzocaine, cocaine, chlorprocaine, lidocaine, bupivocaine, procaine).

As used herein the specification, "a" or "an" may mean one or more. As used herein in the claim(s), when used in a period of 30 minutes (the reaction mixture starts getting darker as the addition progresses). The resulting dark mixture was stirred overnight (ca. 16 h) and allowed to warm from −78° C. to room temperature. The reaction was quenched by addition of HCl (1 N, 250 mL) at 0° C. The layers were separated, and the aqueous phase was further extracted with ether (3×100 mL). The combined organic extract was washed sequentially with 75 mL portions of saturated $NaHCO_3$, water (several times), and brine, and dried over $MgSO_4$. The solvent was removed in vacuo to give 27.77 g of dark colored liquid. After two vacuum distillations, the nitrile (12.35 g, 45%) was obtained as a colorless liquid: bp 84–85° C. (1.3 mm Hg). An analytical sample was prepared by column chromatography over silica gel (hexanes-EtOAc, 19:1) followed by bulb-to-bulb distillation (pot temp. 80° C. (1 mm Hg)).

EXAMPLE 2

Anesthetic Properties of Diethyl Lactam

Female ICR mice, weighing between 18 and 31 g were used for all experiments. The animals were housed four in a cage in a 24-hour light/dark cycle with free access to food and water. Animal weight at the time of the experiment ranged from 22 to 33 g. On the day of the experiment, animals were brought to the lab in groups of 6–8. They were not allowed food or water for the duration of the testing period. After each experiment, animals were sacrificed.

Diethyl lactam was synthesized as described previously (Example 1 and U.S. Pat. Nos. 6,066,666 and 5,776,959) and dissolved in 0.9% saline. All drugs were given by intraperitoneal (i.p.) injections in a volume of 0.01 ml/g body weight.

The anesthetic effect was determined using the loss of righting reflex (LORR) model of anesthesia. In the test, animals were observed for sedation following injection of the lactam. At the onset of sedation, animals were placed on their back, and if they did not place all four paws on the table surface within one minute, they were considered to have lost their righting reflex. The time to onset and duration of loss of righting reflex was recorded for each animal.

Animals were given diethyl lactam at doses of 250, 325, 375, 500, 625, 750, 875 and 1000 mg/kg of body weight, and the time to regain the righting reflex (RR) as well as the duration of LORR were measured (Table 1). During the experiment, animals given a dosage of 500 mg/kg were observed to have various physical movements. Three of the five mice were seen to twitch. Other movements include a shiver (one mouse), a head twitch (one mouse), face vibrations (one mouse) and repetitive hindlimb scratching (one mouse).

TABLE 1

Dose Response for DiethylABL:LORR Experiment

| Dose (mg/kg) | Number of Trials | LORR (min) | Regain RR (min) | Duration of LORR (min) |
|---|---|---|---|---|
| 250 | 3 | none at 30 min | — | 0 |
| 325 | 3 | none at 30 min | — | 0 |
| 375 | 5 | none at 30 min | — | 0 |
| 500 | 5 | 2.4 ± 1.8 | 41 ± 12 | 38.8 ± 11.6 |
| 625 | 10 | 1.7 ± 0.8 | 53 ± 16 | 51.3 ± 16.2 |
| 750 | 3 | 0.9 ± 0.3 | 110 ± 2 | 109.7 ± 2.0 |
| 875 | 3 | 0.8 | >360 | >360 |
| 1000 | 2/2 | 2.0 ± 2.1 | 1470 ± 85 | 1470.0 ± 756 |

Error bars are one standard deviation.

Two mice given 1000 mg/kg were excluded from the trial as outliers, having LORR at 2.4 and 4.2 min, regaining RR at 159 and 174.5 min for a LORR duration of 156.6 and 170.3 min respectively. Two mice given 1000 mg/kg which were included in the trial died 7.3 and 4.0 minutes after injection.

PROPHETIC EXAMPLE 3

Methods for Anesthetizing Human Subjects

The lactam and thiolactam derivatives can be administered to a human subject to induce anesthesia or conscious sedation. For example, a human patient may be given an injection containing diethyl lactam at a concentration of between 10 mg/kg and 1000 mg/kg body weight dissolved in a 0.9% saline solution. The dose of the drug will also determine the duration of the anesthesia. This injection can be given immediately before the subject must be under anesthesia. Recovery from anesthesia will be rapid.

Conscious sedation may be induced in a human subject by injecting a solution containing diethyl lactam. A concentration of between 1 mg/kg and 100 mg/kg body weight will be given as appropriate. The onset of conscious sedation should be immediate, and the duration can be adjusted by administering repeat dose(s). Recovery from conscious sedation will be rapid.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams et al. (Sep. 20, 1959) "The Absolute configuration of the C1 Atom in Retronecanone (1-Methyl-7-oxopyrrolizidine)," J. Am. Chem. Soc. 81:4946–4951.

Baker J A, Harper J F (1967) "Synthesis of 3,3-diethylpiperid-2-one" J. Chem. Soc., C, 2148.

Bentz G, Besbes N, Laurent A, Stamm H (1987) "Intramolecular radical trapping in SET ring opening of N-(enoyl) aziridines. A new mechanistic probe and a new synthesis of pyrrolidones" Tetrahedron Lett., 28, 2511–2512.

Bodine J J and Kaloustian M K (1982) "An Efficient Conversion of N-Alkyllactams to N-Alkylthiolactams" Synthetic Comm. 12(10) 787–793.

Brunner O, Heck-Bleckmann Chr (1951) "Uber das 3-athylpyrrolidin und einige derivate" Monatsh., 82, 371–376.

Callery, P. S. et al. (1984), "Biosynthesis of 5-Aminopentanoic Acid and 2-Piperidone from Cadaverine and 1-Piperidone in Mouse," J. Neurochem. 43:(6):1631–1634.

Camu F. "Why should I change my practice of anesthesia? Opioids" Minerva Anestesiol 2000 May; 66(5):268–72

Canney et al. (1991), "Synthesis and Structure-Activity Studies of Alkyl-Substituted -Butyrolactones and -Thiobutyrolactones: Ligands for the Picrotoxin Receptor," J. Med. Chem., 34:1460–1467.

Carter P A, Singh S "Preparation of di- and trisubstituted piperidines, morpholines, and bromopiperidines as agrochemical fungicides" Eur. Pat. Appl. EP 435,387. Jul. 3, 1991.

Colombo et al. (1991), "Chemoenzymatic Synthesis of the Enantiomers of Iopanoic Acid," Tetrahedron: Asymmetry 2(10):1021–1030.

Cummings et al. (1963), "The Synthesis and Rearrangement of 3-Vinyl-2-pyrrolidone," British Nylon Spinners Ltd., Research Department, Pontypool, Monmouthsire, UK, pp. 4591–4604.

Cummings W A W, Davis A C (1964) "The synthesis and rearrangement of 3-vinyl-2-pyrrolidone" J. Chem. Soc., 4591–4604.

EP 0151964 A2 Aug., 1985

EP 0435387 A1 Jul., 1991

EP 435,387 (Carter P A and Singh S, published 1991)

Feiss P. "New halogenated agents: should I change my practice?" Minerva Anestesiol 2000 May; 66(5):264–7

Geurtis et al. (1977), "2-Pyrrolidinones," Chem. Abst., vol. 86, 29622r, p350.

Geurtis L H, Meyer P J N "2-Pyrrolidinones" Ger. Offen. 2,609,209 Sep. 16, 1976 and Chem. Abst. (1977) 86, 29622r.

Goodman and Gilman's "The Pharmacological Basis of Therapeutics," 9th Ed., 1996, MacMillan, New York, Chapters 13–15.

Hamill et al. (1981), "Improved Patch-Clamp Techniques for High-Resolution Current Recording from Cells and Cell-Free Membrane Patches," Pflugers Arch. 391:85–100.

Hill, M. W. et al. (1998a) "Contribution of Subsaturating GABA Concentrations to IPSCs in Cultured Hippocampal Neurons" J. of Neuroscience 18(14) 5103–5111.

Hill, M. W. et al. (1998b) "Inhibition of Voltage-Dependent Sodium Channels by the Anticonvuslant γ-Aminobutyric Acid Type A1 Receptor Modulator, 3-Benzyl-3-Ethyl-2-Piperidinone" J. Pharmacol. Exp. Ther. 285, 1303–1309.

Hill, M. W. et al. (1999), "Effects of anticonvulsant lactams on in vitro seizures in the hippocampal slice preparation." Epilepsy Research, 37, 121–131.

Holland et al. (1990), "-Butyrolactone Antagomism of the Picrotoxin Receptor: Comparison of a Pure Antagonist and a Mixed Antagonist/Inverse Agonist," Mol. Pharmacology, 39:79–84.

Holland et al. (1990), "Physiological Regulation of the Picrotoxin Receptor by -Butyrolactones and -Thiobutyrolactones in Cultured Hippocampal Neurons," J. Neurosci., 10(6):1719–1727.

Jackman, L. M. et al. (1982), J. Org. Chem., pp. 1824–1831.

Kametani T, Ihara M, Honda T (1970) "Alkaloids of Corydalis pallida var tenuis and the structures of pallidine and kikemanine" J. Chem. Soc. C, 1060–1064.

Khoukhi N, Vaultier M, Carrie, R (1987) "Synthesis and reactivity of methyl-azidobutyrates and ethyl-azidovalerates and of the corresponding acid chlorides as useful reagents for the aminoalkylation" Tetrahedron, 43, 1811–1822.

Kircheldorf, H. R. (1975), "Reactions with silylazides. 7. Trimethylsilyl 4-isocyanato-carboxylates and 4-aminocarboxylic acid N-carboxylic acid anhydrides," Makromol. Chem. 176:57–79.

Klunk et al. (1982), "Structure-Activity Relationships of Alkyl-Substituted Butyrolactones and Succinimides," Mol. Pharm., 22:444–450.

Koelsch, C. F. (1943), "A Synthesis of 3-Alkylpiperidones," J. Am. Chem. Soc. 65:2458–2459.

Kricheldorf E I R (1975) "Reactions with silylazides. 7. Trimethylsilyl 4-isocyanato-carboxylates and 4-aminocarboxylic acid N-carboxylic acid anhydrides" Makromol. Chem., 176, 57–79.

Laycock, G. M. et al. (1963) Nature, pp. 849–851.

Lion et al. (1981), "Alkylation of some carbonyl compounds by tertiary alkyl groups. Utilization of the Friedel-Crafts reaction in the synthesis of sterically crowded esters and ketones," Tetrahedron, 37:319–323.

Lister, R. G. (1987), "The use of a plus-maze to measure anxiety in the mouse," Psychopharm. 92:180–185.

Menezes R, Smith M B (1988) "A mild and facile root to-amino esters" Syn. Commun., 18, 1625–1636.

Meyers et al. (1987), "Conformational Effects on the Regiochemical Metalation of $C_5$–$C_13$ N-Benzyllactams," J. Am. Chem. Soc. 109: 4405–4407.

Mileo J C, Sillion B, De Gaudemaris G. "3,3-Dimethyl-2-pipemdinone" Fr. 1,527,755, Jun. 7, 1968.

Potts K T, Rochanapruk T, Coats S J, Hadjiarapoglou L, and Padwa A (1993) "Intramolecular 1,4-Dipolar Cycloaddition of Cross-Conjugated Heterocyclic Betains. A New Route to Hexahydrojulolidines and Related Peri-Fused Ring Systems" J. Org. Chem. 58 5040–5042.

Quast et al. (1986), "Photochemical formation of methylenecyclopropane analogs. XII. Synthesis of 3,5,5-trialkyl-3,5-dihydro-4H-1,2,3-triazol-4-ones," Liebigs Ann. Chem. pp. 1891–1899.

Reddy, P. A. et al., (1996) "3,3-Dialkyl- and 3-alkyl-3-benzyl-substituted 2-pyrrolidinones: a new class of anticonvulsant agents" J. Med. Chem. 39, 1898–1906.

Reddy, P. A. et al., (1997) "Synthesis and anticonvulsant activities of 3,3-dialkyl- and 3-alkyl-3-benzyl-2-piperidinones (δvalerolactams) and hexahydro-2H-azepin-2-ones (ε-caprolactams" J. Med. Chem. 40, 44–49.

Rodriguez M, Heitz A, Martinez J (1992)"Carba peptide bond surrogates. Different approaches to Gly-(CH2-CH2)-D, L-Xaa pseudo-dipeptide units" Int. J. Peptide Protein Res. 39, 273–277.

Sinnerich J, Elad D (1968) "The light-induced addition of 2-pyrrolidinone to olefins" Tetrahedron, 24, 4509–4516.

Spencer et al. (1986), "Ynenol Lactones: Synthesis and Investigation of Reactions Relevant to Their Inactivation of Serine Proteases," J. Am. Chem. Soc., 108:5589–5597.

Stamm et al. (1981), "Reactions with aziridines. XXII. One step synthesis of pyrrolidones by amidoethylation of simple esters with N-acylaziridines," Chem. Ber. 114:32–48.

Swinyard et al. (1982), "Experimental Detection, Quantification, and Evaluation of Anticonvulsants," Anti-epileptic Drugs, Woodbury, Pentry and Pippenger, eds., Raven Press, NY, pp. 111–126.

Trevor, A. J. and Way. W. L. (1992), "Sedative-hypnotics" Basic & linical Pharmacology, Katzung, B. G., Ed., Appleton & Lnage, Norwalk, Conn., 5th Ed., pp. 306–319.

U.S. Pat. No. 5,776,959
U.S. Pat. No. 6,066,666

Wang C H J, Stroupe S D, Jolley M E "Fluorescent polarization immunoassay utilizing substituted triazinylaminofluoresceins" U.S. Pat. No. 4,420,568 Dec. 13, 1983.

Werry J, Stamm H, Lin P Y, Falkenstein R, Gries S, Irngartnger H (1989) "Reactions with aziridines. Part 50. Homolytic aziridine ring opening (aza variant of cyclopropylcarbinyl-homoallyl rearrangement) by addition of tributyltin radical to N-acylaziridines. Factors contributing to the regioselectivity" Tetrahedron, 45, 5015–5028.

Whitwam, J G (1995) "Co-induction of anaesthesia: day-case surgery" Eur. J. Anaesthesiol Suppl 12:25–34.

Yamaguchi et al. (1985), "A Direct Synthesis of [(tert-Butoxycarbonyl)-methylidene]-azacycloalkanes from N-Alkyl Lactams," J. Org. Chem. 50:1975–1977.

Yoon, Kong-Woo et al. (1990), "Modulation of the Picrotoxin Receptor by Fluorinated Ethyl, Methyl-Butyrolactones1," J. Pharmacol. Exp. Ther, 255(1):248–255.

What is claimed is:

1. A method for inducing anesthesia or conscious sedation in a patient in need thereof comprising administering to the patient a composition comprising a compound having the formula:

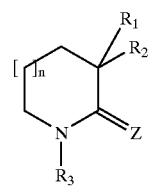

or pharmaceutically acceptable salts thereof wherein:
n is 0 or 1;
Z is an O or S; and $R_1$, $R_2$, and $R_3$ are independently selected from the group consisting of H, an optionally substituted alkyl or alkenyl group, and an optionally substituted phenylmethyl group, with the exceptions that: $R_1$ and $R_2$ cannot both be H; when one of $R_1$ or $R_2$ is H or a methyl group, the other of $R_1$ or $R_2$ cannot be a methyl or ethyl group; and when n=1, $R_1$ and $R_2$ cannot both be ethyl.

2. The method of claim 1, wherein said compound has a water solubility of between 0.1 g per 1.0 g of water and the point of saturation.

3. The method of claim 2, wherein said compound has a water solubility of between 0.5 g per 1.0 g of water and the point of saturation.

4. The method of claim 3, wherein said compound has a water solubility of between 1.0 g per 1.0 g of water and the point of saturation.

5. The method of claim 1, wherein said composition comprises water or buffer.

6. The method of claim 1, wherein said compound is administered intravenously.

7. The method of claim 1, wherein said compound is administered orally.

8. The method of claim 1, wherein said compound is administered rectally, intramuscularly, subcutaneously, or through an inhalation administration.

9. The method of claim 1, wherein said compound is given at a dosage of from 1–1000 mg/kg.

10. The method of claim 9, wherein said compound is given at a dosage of from 100–1000 mg/kg.

11. The method of claim 9, wherein said compound is given at a dosage of from 10–100 mg/kg.

12. The method of claim 1, wherein said compound is in an enantiomerically enriched mixture.

13. The method of claim 1, wherein said compound is 3,3-diethyl-2-pyrrolidinone.

14. The method of claim 1, wherein said compound produces an onset of anesthesia in less than 5 minutes after administration.

15. The method of claim 14, wherein said compound produces an onset of anesthesia in less than 1 minute after administration.

16. The method of claim 15, wherein said compound produces an onset of anesthesia in less than 10 seconds after administration.

* * * * *

UNITED STATES PATENT AND TRADEMARK OFFICE
CERTIFICATE OF CORRECTION

PATENT NO. : 6,680,331 B2  Page 1 of 1
APPLICATION NO. : 09/907547
DATED : January 20, 2004
INVENTOR(S) : James A. Ferrendelli et al.

It is certified that error appears in the above-identified patent and that said Letters Patent is hereby corrected as shown below:

In column 1, lines 5-7, delete
"The government may own rights in the present invention pursuant to grant number 5 PO1 NS14834 from the National Institute of Health." and insert
--This invention was made with government support under grant number NS014834 awarded by the National Institutes of Health. The government has certain rights in the invention.-- therefor.

Signed and Sealed this

Fifth Day of May, 2009

JOHN DOLL
*Acting Director of the United States Patent and Trademark Office*